United States Patent
Feldman

(10) Patent No.: US 9,423,404 B1
(45) Date of Patent: Aug. 23, 2016

(54) METHOD OF SCREENING FOR AN AGENT THAT ENHANCES BEIGE FAT ADIPOGENESIS

(71) Applicant: The Board of Trustees of the Leland Stanford Junior University, Palo Alto, CA (US)

(72) Inventor: Brian Jay Feldman, Stanford, CA (US)

(73) Assignee: The Board of Trustees of the Leland Stanford Junior Unviversity, Stanford, CA (US)

( * ) Notice: Subject to any disclaimer, the term of this patent is extended or adjusted under 35 U.S.C. 154(b) by 0 days.

(21) Appl. No.: 14/205,170

(22) Filed: Mar. 11, 2014

Related U.S. Application Data

(60) Provisional application No. 61/782,301, filed on Mar. 14, 2013.

(51) Int. Cl.
- *G01N 33/50* (2006.01)
- *G01N 33/82* (2006.01)
- *C12N 15/113* (2010.01)
- *C07K 14/705* (2006.01)

(52) U.S. Cl.
CPC ............ *G01N 33/82* (2013.01); *C12N 15/1138* (2013.01); *G01N 33/5023* (2013.01); *G01N 33/5041* (2013.01); *G01N 33/5044* (2013.01); *G01N 33/5073* (2013.01); *C07K 14/70567* (2013.01)

(58) Field of Classification Search
None
See application file for complete search history.

(56) References Cited

PUBLICATIONS

Polly et al, 2000. FASEB J. 1455-1463.*
Blumberg et al, 2006. Journal of Biological Chemistry, 281(16):11205-11213.*
Ferrarezi et al., "Allelic variations in the vitamin D receptor gene, insulin secretion and parents' heights are independently associated with height in obese children and adolescents", Metabolism (Apr. 2012), 61(10):1413-1421.
Sun et al., "p38 MAPK regulates calcium signal-mediated lipid accumulation through changing VDR expression in primary preadipocytes of mice", Mol Biol Rep (2012), 39(3):3179-3184.
Wong et al., "Involvement of the vitamin D receptor in energy metabolism: regulation of uncoupling proteins", Am J Physiol Endocrinol Metab (2009), 296(4):E820-E828.
Wong et al., "Targeted Expression of Human Vitamin D Receptor in Adipocytes Decreases Energy Expenditure and Induces Obesity in Mice", J Biol Chem (2011), 286(39):33804-33810.
Zitman-Gal et al., "Vitamin D receptor activation in a diabetic-like environment: potential role in the activity of the endothelial pro-Inflammatory and thioredoxin pathways", J Steroid Biochem Mol Biol (2012), 132(1-2):1-7.

* cited by examiner

*Primary Examiner* — Zachary Howard
(74) *Attorney, Agent, or Firm* — Pamela J. Sherwood; Bozicevic, Field & Francis LLP

(57) ABSTRACT

Methods and compositions are provided for enhancing beige fat adipogenesis, and screening for agents having this activity An adipocyte progenitor cell is contacted with an effective dose of an antagonist of unliganded vitamin D receptor (VDR) activity. The contacting may be performed under adipogenic conditions.

5 Claims, 4 Drawing Sheets
(2 of 4 Drawing Sheet(s) Filed in Color)

METHOD OF SCREENING FOR AN AGENT THAT ENHANCES BEIGE FAT ADIPOGENESIS

FEDERALLY SPONSORED RESEARCH AND DEVELOPMENT

This invention was made with Government support under contract OD006740 awarded by the National Institutes of Health. The Government has certain rights in the invention.

BACKGROUND OF THE INVENTION

Obesity is a widely prevalent body weight disorder, affecting an estimated 30 to 50% of the middle-aged population in the western world. Obesity, defined as a body mass index (BMI) of 30 or more, contributes to diseases such as coronary artery disease, hypertension, stroke, diabetes, hyperlipidemia and some cancers. It is a complex multifactorial chronic disease that develops from an interaction of genotype and the environment and involves social, behavioral, cultural, physiological, metabolic and genetic factors.

Adipose tissue consists primarily of adipocytes. Vertebrates possess two distinct types of adipose tissue: white adipose tissue (WAT) and brown adipose tissue (BAT), which has a phenotype in adult humans commonly referred to as "beige" fat. WAT stores and releases fat according to the nutritional needs of the animal. This stored fat is used by the body for heat insulation, mechanical cushioning, and as a source of energy. BAT burns fat, releasing the energy as heat through thermogenesis. BAT thermogenesis is used both to maintain homeothermy by increasing thermogenesis in response to lower temperatures and to maintain energy balance by increasing energy expenditure in response to increases in caloric intake. In humans, and to a lesser extent rodents, brown fat diminishes with age, but can be re-activated under certain conditions.

In the development of obesity, an increase in adipose tissue mass can be due to an increase in both the size (hypertrophic growth) and number (hyperplastic growth) of adipocytes. Hypertrophic growth is an increase in size of adipocytes stimulated by lipid accumulation. Hyperplastic growth is defined as an increase in the number of adipocytes in adipose tissue, for example as result of recruitment of preadipocytes from a population of multipotent stem cells or from subpopulations of cells resident in mature white adipose tissue (WAT). It is thought to occur primarily by mitosis of pre-existing adipocytes caused when adipocytes fill with lipid and reach a critical size. An increase in the number of adipocytes has far-reaching consequences for the treatment and prevention of obesity.

Current therapies for obesity predominantly lead to decreased energy intake by acting at satiety centers in the brain or by reducing the efficiency of intestinal absorption. To date, no safe and reliable molecular mechanism has been found for treating and/or preventing obesity by altering the composition of adipose tissues to generate more brown fat cells. Given the severity and prevalence of obesity related disorders, there exists a great need for the identification of an anti-obesity therapeutic.

SUMMARY OF THE INVENTION

Methods are provided for screening candidate agents for activity in enhancing brown/beige fat adipogenesis by interfering with unliganded VDR repression of UCP1 expression. Screening assays of interest include determining the effectiveness of an agent on the occupancy of UCP1 VDRE4; effect of an agent on expression of UCP1 in cells under apidipogenic conditions; design of agents to interfere with VDR H305 region; and the like. Candidate antagonists include, without limitation, monoclonal antibodies, small molecules, chimeric proteins/peptides, bioactive polypeptides, and nucleic acids, e.g. RNAi and antisense nucleic acids that interfere with VDRE4, etc.

An antagonist of unliganded VDR activity identified by the screening methods of the invention may be provided in a pharmaceutical formulation suitable for administration to a patient. Formulations of interest include, without limitation, formulations for systemic administration, including parental administration. Alternatively formulations of interest provide for substantial retention of the agent in a tissue of interest, e.g. in adipose tissue and the like.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE SPECIFIC EMBODIMENTS

Figure 1:
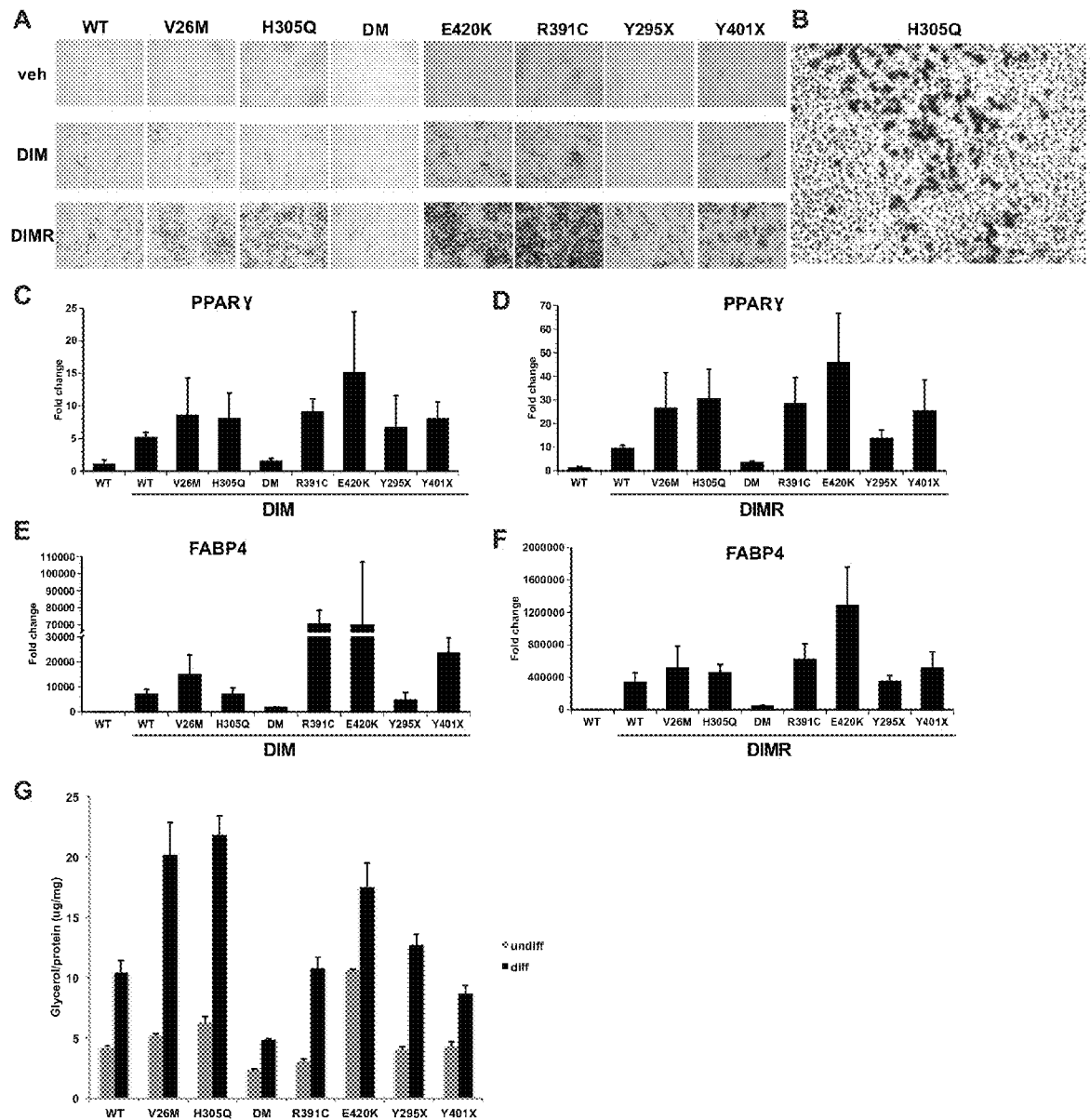
FIG. 1. Differentiated human fibroblasts have small multilocular lipid droplets and exhibit functional properties of adipocytes. (A) Human fibroblasts were treated with vehicle, DIM or DIM plus rosiglitazone for 14 days and examined by light microscopy. (B) Oil red O positive staining was evident in the HVDRR cells (H305Q) treated DIM plus rosiglitazone indicating the presence of lipids. Relative gene expression of PPARγ and FABP4 treated with DIM (C and E) or DIMR (D and F) compared to vehicle control. (G) Glycerol release in the supernatant of human skin fibroblasts treated with vehicle (undiff) or differentiated (diff) with DIMR adipogenic media following treatment with isoproterenol. The quantity of glycerol released (in micrograms) was normalized to the total amount of protein (in milligrams) for each sample. Three independent experiments were performed. Error bars represent standard deviation from the mean (s.d.).

Screening methods are provided to identify candidate reagents that will enhance thermogenesis associated with brown/beige fat or brown/beige fat cells. Candidate agents of interest comprise an effective dose of an antagonist of unliganded VDR activity, i.e. activity that is independent of vitamin D binding. Such agents are effective in relieving repression of UCP1 protein expression during adipogenesis, where, for example, levels of UCP1 protein in adipocytes, e.g. nascent adipocytes, targeted by the methods of the invention, may be increased at least 2-fold, at least 5-fold, at least 10-fold, at least 20-fold or more relative to the level of UCP1 protein in untreated cells under the same conditions. Antagonists include, without limitation, monoclonal antibodies, small molecules, chimeric proteins/peptides, bioactive polypeptides, and nucleic acids, e.g. RNAi and antisense nucleic acids that interfere with VDRE4, etc.

Inhibition of unliganded VDR activity, particularly including inhibition of VDR occupancy of VDRE4 of UCP1, alters energy metabolism and metabolic efficiency in an individual by modulating thermogenesis by brown/beige adipose tissue (BAT). More specifically, regulation of thermogenesis by brown/beige fat includes but is not limited to thermogenesis, adaptive thermogenesis and thermogenic capacity. Thermogenesis is the process of heat production in organisms. Thermogenesis encompasses those processes initiated through locomotion and intentional movement of the muscles, including but not limited to exercise-associated thermogenesis, non-exercise activity thermogenesis, and diet-induced thermogenesis.

In some embodiments, an adipocyte or adipocyte progenitor cell is cultured in vitro, for example where a cell is maintained in adipogenic conditions, e.g. in the presence of an adipogenic cocktail such as dexamethasone, insulin, IBMX (1-Methyl-3-isobutylxanthine, 3,7-Dihydro-1-methyl-3-(2-methylpropyl)-1H-purine-2,6-dione, 3-isobutyl-1-methyl-2,6(1H,3H)-purinedione) (DIM) alone or in combination with the PPARγ agonist rosiglitazone (DIMR). Such in vivo generated cells have utility in screening assays, for generating beige fat calls for research and screening purposes, and to generate therapeutically useful brown/beige fat cells.

DEFINITIONS

In the description that follows, a number of terms conventionally used in the field of cell culture and adipogenesis are utilized extensively. In order to provide a clear and consistent understanding of the specification and claims, and the scope to be given to such terms, the following definitions are provided.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "an", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The term "adipocyte" refers to a fat cell, which may be a white fat cell, a brown fat cell, or a beige fat cell. In adult life there can be a turnover in fat cells as a result of acquisition of new adipocytes from adult adipose tissue progenitors (mesenchymal stem cells and preadipocytes) via adipogenesis. Conditions in which adipogenesis is undesirable can include obesity, metabolic syndrome and Type 2 diabetes; and the like. It is shown herein that an antagonist of unliganded vitamin D receptor (VDR) activity will, under adipogenic conditions, enhance brown/beige fat formation, e.g. during reprogramming of fibroblasts to adipocytes, during adipogenesis in vivo, and the like. Administration of the agent in an effective dose to an individual in need thereof provides for an altered ratio of white and brown/beige fat, where thermogenesis is increased, resulting in a decrease of obesity.

Adipocyte progenitor cells in vivo have been described in the art as including mesenchymal stem cells (MSC), multipotent adipose progenitor cells, pre-adipocytes and early adipocytes. A cell may be classified as an MSC if it shows plastic adherent properties under normal culture conditions and has a fibroblast-like morphology, can undergo osteogenic, adipogenic and chondrogenic differentiation ex-vivo; and is positive for CD73, CD90 and CD105, while lacking the expression of CD11 b, CD14, CD19, CD34, CD45, CD79a and HLA-DR surface markers. Multipotent adipose progenitors have been described as Lin−, CD29+, CD34+, CD24+(see Lin et al. (2008) Stem Cells Dev. 17:1053-1063). Early adipocyte progenitor cells have been described as Lin−, CD29+, CD34+, CD24+ (see Rodeheffer et al. (2008) Cell 135:240-249). resident in adult WAT. Immature adipocyte or preadipocytes have been described as aP2+/CD68−. Adipose tissue-derived stem cells (ADSC) are routinely isolated from the stromal vascular fraction (SVF) of homogenized adipose tissue. Freshly isolated ADSC display surface markers that differ from those of cultured ADSC, but both cell preparations are capable of multipotential differentiation.

Brown, or beige, fat is one of two types of fat or adipose tissue found in mammals (the other being white adipose tissue). Brown or beige fat is present in most if not all mammals, including humans, and is especially abundant in newborns and in hibernating mammals. In contrast to white adipocytes, which contain a single lipid droplet, brown or beige adipocytes contain numerous smaller droplets and a much higher number of mitochondria, which contain iron and account for the brown color. BAT cells are smaller than normal storage cells, contain less fat, and have a high mitochondria content. These mitochondria hold a specialized uncoupling protein, namely uncoupling protein 1 (UCP1, also known as thermogenin), that allows for uncoupling of oxidative phosphorylation, leading to the production of heat but no ATP.

Thermogenesis by brown or beige fat is thought to play a role in the prevention or control of obesity. For example, see Nedergaard and Cannon, 2010, "The changed metabolic world with human brown adipose tissue: therapeutic visions," Cell Metab. 11:268-272; Enerback S. 2010, "Human brown adipose tissue," Cell Metab. 11:248-252; and Tseng et al., 2010, "Cellular bioenergetics as a target for obesity therapy,"

Nature Reviews Drug Discovery 9:465-482, each of which is hereby incorporated by reference herein in its entirety.

Recent years have brought a greater appreciation for potential beneficial effects of acquiring brown fat cells in non-classic BAT locations, such as WAT and skeletal muscle. The presence of brown fat cells in WAT may come from de novo differentiation, or may come from the existing white adipocytes, a process called transdifferentiation. It is likely that both mechanisms co-exist in the body and different stimuli may preferentially activate one pathway over the other.

Phenotyping of brown or beige fat cells relative to white fat cells may utilize any convenient molecular or histological marker(s), for example see Farmer, (2008) Genes Dev. 22(10): 1269-1275, herein specifically incorporated by reference. A "browning" of the white cells can be characterized by an increase in mitochondrial mass and structure as well as a markedly enhanced oxygen consumption and lipid oxidation.

The term "sufficient to enhance BAT adipogenesis" is intended to encompass any inhibition of unliganded VDR activity, including occupancy of UCP1 VDRE4, which promotes, activates, stimulates, enhances, or results in brown or beige fat differentiation. In another aspect, the invention relates to methods for treating obesity or an obesity-related disorder, e.g., Type II diabetes, in a subject comprising administering to the subject an agent that inhibits the unliganded VDR activity and increases respiration and energy expenditure to thereby treat obesity or an obesity-related disorder.

The term "administering" is intended to include routes of administration which allow the agent to perform its intended function of increasing brown or beige fat differentiation. Examples of routes of administration which can be used include injection (subcutaneous, intravenous, parenterally, intraperitoneally, intrathecal, etc.), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. Further the agent may be coadministered with a pharmaceutically acceptable carrier. The agent also may be administered as a prodrug, which is converted to its active form in vivo.

The term "cell culture" or "culture" means the maintenance of cells in an artificial, in vitro environment. Culture conditions may include, without limitation, a specifically dimensioned container, e.g. flask, roller bottle, plate, 96 well plate, etc.; culture medium comprising suitable factors and nutrients for growth of the desired cell type; and a substrate on the surface of the container or on particles suspended in the culture medium. By "container" is meant a glass, plastic, or metal vessel that can provide an aseptic environment for culturing cells.

The terms "primary culture" and "primary cells" refer to cells derived from intact or dissociated tissues or organs, or fragments thereof. A culture is considered primary until it is passaged (or subcultured) after which it is termed a "cell line" or a "cell strain." The term "cell line" does not imply homogeneity or the degree to which a culture has been characterized. A cell line is termed "clonal cell line" or "clone" if it is derived from a single cell in a population of cultured cells. Primary cells can be obtained directly (or indirectly) from a human or animal or from adult or fetal tissue, including blood (e.g., cord blood), muscle tissue, adipose tissue, etc. The primary cells may comprise a primary cell line, such as, but not limited to, a population of muscle satellite cells.

Culture medium: Cells are grown in vitro in an appropriate liquid nutrient medium. Generally, the seeding level will be at least about 10 cells/ml, more usually at least about 100 cells/ml and generally not more than about $10^5$ cells/ml, usually not more than about $10^4$ cells/ml. Cells may be cultured singly or in groups.

Various media are commercially available and may be used, including, but not limited to, Ex vivo serum free medium, Dulbecco's Modified Eagle Medium (DMEM), RPMI, Iscove's medium, etc. The medium may be supplemented with serum or with defined additives. For example, a medium may include 5%, 10%, 15% serum, as known in the art. Appropriate antibiotics to prevent bacterial growth and other additives, including, but not limited to, pyruvate (0.1-5 mM), glutamine (0.5-5 mM), 2-mercaptoethanol ($1\text{-}10\times10^{-5}$ M) may also be included. The medium may be any conventional culture medium, generally supplemented with additives, including, but not limited to, iron-saturated transferrin, human serum albumin, soy bean lipids, linoleic acid, cholesterol, alpha thioglycerol, crystalline bovine hemin, etc., that allow for the growth of cells. In some circumstances, proliferative factors that do not alter cellular differentiation may be included in the cultures, e.g. c-kit ligand, LIF, and the like. Medium may include the presence of an adipogenic cocktail such as dexamethasone, insulin, IBMX (1-Methyl-3-isobutylxanthine, 3,7-Dihydro-1-methyl-3-(2-methylpropyl)-1H-purine-2,6-dione, 3-Isobutyl-1-methyl-2,6(1H,3H)-purinedione) (DIM) alone or in combination with the PPARγ agonist rosiglitazone (DIMR). Medium of interest will may include a candidate antagonist of unliganded VDR activity, although for screening purposes control cultures will also be utilized, and the cultures may have a sub-optimal dose of the agent.

Cultured cells may be modified prior to, or during the culture period. In some embodiments, the cultured cell is a stem cell. In some embodiments, the stem cells are genetically modified for therapeutic or experimental purposes, e.g. by introducing factors that provide for oncogenic transformation, by introducing therapeutic genes such as dystrophin, and the like.

Obesity. In general terms obesity denotes excess body fat; the consequences of which depend not only on the absolute amount but also on the distribution of the fat. Complications include cardiovascular disorders, diabetes mellitus, many cancers, cholelithiasis, fatty liver and cirrhosis, osteoarthritis, reproductive disorders in men and women, psychologic disorders, and premature death. Diagnosis is based on body mass index calculated from height and weight, and waist circumference. BP, fasting plasma glucose, and lipid levels should be measured. Treatment includes physical activity, dietary and behavioral modification, and sometimes drugs or surgery.

Obesity can refer to a body mass index (BMI) of 30 kg/m² or more. However, the present invention is also intended to include a disease, disorder, or condition that is characterized by a body mass index (BMI) of 25 kg/m² or more, 26 kg/m² or more, 27 kg/m² or more, 28 kg/m² or more, 29 kg/m² or more, all of which are typically referred to as overweight. The obesity described herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity or a decrease in resting energy expenditure as a percentage of total fat-free mass.

Heritability of BMI is about 66%. Genetic factors may affect the many signaling molecules and receptors used by parts of the hypothalamus and GI tract to regulate food intake. Rarely, obesity results from abnormal levels of peptides that regulate food intake (eg, leptin) or abnormalities in their receptors (eg, melanocortin-4 receptor). Genetic factors also regulate energy expenditure, including BMR, diet-induced thermogenesis, and nonvoluntary activity-associated thermogenesis. Genetic factors may have a greater effect on the distribution of body fat, particularly abdominal fat, than on the amount of body fat.

Insulin resistance, dyslipidemias, and hypertension (the metabolic syndrome) develop, often leading to diabetes mellitus and coronary artery disease. These complications are more likely in patients with fat that is concentrated abdominally, a high serum triglyceride level, a family history of type 2 diabetes mellitus or premature cardiovascular disease, or a combination of these risk factors.

With aging, body fat increases and is redistributed to the abdomen, and muscle mass is lost, largely because of physical inactivity, but decreased androgens and growth hormone (which are anabolic) and inflammatory cytokines produced in obesity may also play a role.

The terms "metabolic disorder" and "obesity related disorders" are used interchangeably herein and include a disorder, disease or condition which is caused or characterized by an abnormal metabolism (i.e., the chemical changes in living cells by which energy is provided for vital processes and activities) in a subject. Metabolic disorders include diseases, disorders, or conditions associated with aberrant thermogenesis or aberrant adipose cell (e.g., brown, beige or white adipose cell) content or function. Metabolic disorders can detrimentally affect cellular functions such as cellular proliferation, growth, differentiation, or migration, cellular regulation of homeostasis, inter- or intra-cellular communication; tissue function, such as liver function, muscle function, or adipocyte function; systemic responses in an organism, such as hormonal responses (e.g., insulin response).

Methods

The methods of the present invention provide in vitro and screening methods for identifying candidate agents that act as an antagonist of unliganded VDR activity, as described herein, and enhance regulate adipogenesis and metabolism. The agents find use, for example, in ex vivo cultures for generation of brown/beige fat adipocytes. A useful antagonist will usually confer an increase in the number of BAT cells in a targeted population by at least 1%, at least 5%, at least 10%, at least 20% or more relative to an untreated control population, where BAT cells may be quantitated on the basis of any convenient marker as described above.

In Vitro Methods

A population of cells comprising adipose stem cells, pre-adipocytes, white adipose cells, fibroblasts, etc. can be cultured in vitro in the presence of an effective dose of an antagonist of unliganded VDR activity. The cells are maintained in culture for a period of time sufficient to confer a higher degree of differentiation to brown or beige adipocytes. The effect on differentiation may be assayed as described in the examples, for example by assaying cells for the expression of genes and proteins specific for BAT cells; and the like.

After seeding the culture medium, the culture medium is maintained under conventional conditions for growth of mammalian cells, generally about 37° C. and 5% $CO_2$ in 100% humidified atmosphere. The media may comprise an adipogenic cocktail, as described herein. Fresh media may be conveniently replaced, in part, by removing a portion of the media and replacing it with fresh media. Various commercially available systems have been developed for the growth of mammalian cells to provide for removal of adverse metabolic products, replenishment of nutrients, and maintenance of oxygen. By employing these systems, the medium may be maintained as a continuous medium, so that the concentrations of the various ingredients are maintained relatively constant or within a predescribed range. Such systems can provide for enhanced maintenance and growth of the subject cells using the designated media and additives.

Following activation, the cells may be removed from the culture by digestion with enzymes, chelators, etc., as known in the art using time, temperature, concentration and selection of reagents. One of skill in the art can readily perform a simple titration to determine suitable conditions, e.g. using EDTA, elastase; dispase; collagenase; trypsin; blendzyme; and the like.

These cells may find various applications for a wide variety of purposes. The cell populations may be used for screening various additives for their effect on growth and the mature differentiation of the cells. In this manner, compounds which are complementary, agonistic, antagonistic or inactive may be screened, determining the effect of the compound in relationship with other therapies.

Often, a subject provides cells for the use in the methods and compositions disclosed herein. The subject may be free of a disease condition. In other cases, the subject is suffering from, or at high risk of suffering from, a health condition or even an acute health condition. In certain cases, a subject provides cells for his or her future use, e.g., an autologous therapy, or for the use of another subject who may need treatment or therapy, e.g., an allogeneic therapy.

The BAT cells may be administered in any physiologically acceptable excipient, where the cells may find an appropriate site for regeneration and differentiation. The cells may be introduced by injection, catheter, or the like. The cells may be frozen at liquid nitrogen temperatures and stored for long periods of time, being capable of use on thawing. If frozen, the cells will usually be stored in any suitable medium, for example 10% DMSO, 20% FCS, 70% DMEM medium. Once thawed, the cells may be expanded by use of growth factors and/or feeder cells associated with progenitor cell proliferation and differentiation.

The cells can be supplied in the form of a pharmaceutical composition, comprising an isotonic excipient prepared under sufficiently sterile conditions for human administration. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells.

The dosage of the therapeutic formulation will vary widely, depending upon the nature of the condition, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, semi-weekly, or otherwise as needed to maintain an effective dosage level.

Screening

In another aspect of the invention, a method is provided for in vitro screening for agents for relevant inhibition of unliganded VDR activity. Agents of interest may be selective for inhibiting VDR occupancy of VDRE4 of UCP1; may be selective for unliganded VDR activity, etc. Preferred agents have low inhibition of binding of vitamin D and analogs thereof to VDR, and high inhibition of VDR binding to VDRE4 of UCP1. Agents of interest include, but are not limited to, pharmaceutical and genetic agents, e.g. antisense, RNAi, and the like.

A variety of outputs and assays may be measured for this purpose, and in many embodiments a candidate agent will be tested in different assays to confirm activity. For example cell-based assays may include, for example testing for differentiation of cells under adipogenic conditions to brown/beige or white adipocyte phenotypes in the absence or presence of a candidate agent. Biochemical assays may determine the ability of an agent to block binding of VDR to at least one VDR responsive element present in the UCP1 gene, for example VDRE1, VDRE2, VDRE3, VDRE4, particularly VDRE4. Biochemical assays may utilize any other determination of unliganded VDR activity.

A reporter assay, e.g. a luciferase reporter assay, may be utilized based on the binding of VDR to a nucleic acid that contains a relevant VDRE, e.g. VDRE4 described herein. Various formats may be envisioned, where a reporter molecule is bound to either of the VDR or the VDRE, and the binding between the two is determined by retention of the reporter and signal from the reporter. Such assays can be conveniently, although not necessarily, performed as a high throughput assay, For purposes of the assay methods the VDR may be provided as an isolated protein with various polymorphisms that affect function, including without limitation the VDR mutant proteins disclosed herein. Alternatively the VDR protein is present in the context of a cell. Any convenient format may be used for the assay, e.g. wells, plates, flasks, etc., preferably a high throughput format, such as multi-well plates. A test agent of interest is added to the reaction mixture with the VDR protein, for example in the presence of a VDR ligand, a DNA sequence that can be occupied by VDR, etc., usually in different concentrations, and the effect of the agent on VDR occupancy of VDRE in the absence of a VDR ligand such as calcitriol determined.

A variety of different test agents may be screened. Candidate agents encompass numerous chemical classes, e.g., small organic compounds having a molecular weight of more than 50 daltons and less than about 10,000 daltons, less than about 5,000 daltons, or less than about 2,500 daltons. Test agents can comprise functional groups necessary for structural interaction with proteins, e.g., hydrogen bonding, and can include at least an amine, carbonyl, hydroxyl or carboxyl group, or at least two of the functional chemical groups. The test agents can comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Test agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Moreover, screening may be directed to known pharmacologically active compounds and chemical analogs thereof, or to new agents with unknown properties such as those created through rational drug design.

In some embodiments, test agents are synthetic compounds. A number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods.

In another embodiment, the test agents are provided as libraries of natural compounds in the form of bacterial, fungal, plant and animal extracts that are available or readily produced. Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In some embodiments, the test agents are organic moieties. In this embodiment, test agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present invention.

As used herein, the term "determining" refers to both quantitative and qualitative determinations and as such, the term "determining" is used interchangeably herein with "assaying," "measuring," and the like.

In some embodiments test agents are assessed for any cytotoxic activity it may exhibit toward a living eukaryotic cell, using well-known assays, such as trypan blue dye exclusion, an MTT (3-(4,5-dimethylthiazol-2-yl)-2,5-diphenyl-2H-tetrazolium bromide) assay, and the like. Agents that do not exhibit significant cytotoxic activity are considered candidate agents.

A variety of other reagents may be included in the screening assay. These include reagents like salts, neutral proteins, e.g. albumin, detergents, etc., including agents that are used to facilitate optimal binding activity and/or reduce non-specific or background activity. Reagents that improve the efficiency of the assay, such as protease inhibitors, nuclease inhibitors, anti-microbial agents, etc. may be used. The components of the assay mixture are added in any order that provides for the requisite activity. Incubations are performed at any suitable temperature, typically between 4° C. and 40° C. Incubation periods are selected for optimum activity, but may also be optimized to facilitate rapid high-throughput screening. In some embodiments, between 0.1 hour and 1 hour, between 1 hour and 2 hours, or between 2 hours and 4 hours, will be sufficient.

Assays of the invention include controls, where suitable controls include a sample (e.g., a sample comprising VDR protein in the absence of the test agent, in the presence of a VDR ligand, in the absence or presence of a VDRE genetic sequence, etc.) Generally a plurality of assay mixtures is run in parallel with different agent concentrations to obtain a differential response to the various concentrations. Typically, one of these concentrations serves as a negative control, i.e. at zero concentration or below the level of detection.

In some embodiments, a test agent that inhibits VDR occupancy of a VDRE is further tested for its ability to enhance BAT adipogenesis in a cell-based assay. In these embodiments, a test agent of interest is contacted with a mammalian cell capable of adipogenesis; and the effect, if any, of the test agent on BAT adipogenesis is determined.

In another embodiment, agents are identified in a method wherein a cell is contacted with a candidate compound and the expression of UCP1, e.g., mRNA or polypeptide levels, in the cell is determined. The level of expression of UCP1 mRNA or polypeptide levels in the presence of the candidate compound is compared to the level of expression of UCP1 mRNA or polypeptide in the absence of the candidate compound. The candidate compound can then be identified based on this comparison. For example, when expression of UCP1 mRNA or polypeptide in adipocytes is greater (statistically significantly greater) in the presence of the candidate compound than in its absence, the candidate compound is identified as an agent that inhibits unliganded VDR activity. Alternatively, when expression of UCP1 mRNA or polypeptide is less (statistically significantly less) in the presence of the candidate compound than in its absence, the candidate compound is likely not an agent that inhibits unliganded VDR activity.

In another aspect, the invention pertains to a combination of two or more of the assays described herein. For example, a test compound can be identified using a cell-based or a cell-free assay, and the ability of the agent to stimulate BAT differentiation can be confirmed in vivo, e.g., in an animal such as an animal model for obesity or diabetes. Examples of animals that can be used include the transgenic mouse described in U.S. Pat. No. 5,932,779 that contains a mutation in an endogenous melanocortin-4-receptor (MC4-R) gene; animals having mutations which lead to syndromes that include obesity symptoms, the mouse tubby phenotype characterized by maturity-onset obesity; the obese Zucker rat (ZR), a genetic model of human youth-onset obesity and type 2 diabetes mellitus, mice null for the adipocyte fatty acid binding protein, the fat mouse; or animals having mutations which lead to syndromes that include diabetes. Other examples of animals that may be used include non-recombinant, non-genetic animal models of obesity such as, for example, rabbit, mouse, or rat models in which the animal has been exposed to either prolonged cold or long-term overeating.

This invention further pertains to novel agents identified by the above-described screening assays. Accordingly, it is within the scope of this invention to further use an agent identified as described herein in an appropriate animal model. For example, an agent that induces BAT adipogenesis identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Monitoring the influence of agents (e.g., drugs) on obesity and obesity-related disorders can be applied not only in basic drug screening, but also in clinical trials. In such clinical trials, the content of BAT cells in a targeted tissue can be used as a "read out." In addition, genes that are modulated in cells by treatment with the putative agent can be identified. Thus, to study the effect of agents on obesity and obesity-related disorders, for example, in a clinical trial, cells can be isolated and RNA prepared and analyzed for the levels of expression of UCP1 and other genes implicated in BAT adipogenesis. The levels of gene expression (e.g., a gene expression pattern) can be quantified by northern blot analysis or RT-PCR, or alternatively by measuring the amount of polypeptide produced, by any convenient method, or by measuring the levels of activity of VDR, UCP1, or other genes. In this way, the gene expression pattern can serve as a marker, indicative of the physiological response of the cells to the agent. Accordingly, this response state may be determined before, and at various points during treatment of the individual with the agent.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Experimental

Human HVDRR Dermal Fibroblasts can be Differentiated into Adipocyte-Like Cells. To test the impact of VDR on adipocytes in humans, we used an ex vivo model of adipogenesis by differentiating human skin fibroblasts. We examined the role of VDR using our collection of primary cells obtained from patients with HVDRR with several different loss-of-function mutations in VDR (in Table I below).

TABLE 1

| VDR Mutation | Functional Defect | Reference |
|---|---|---|
| V26M | DNA binding | Malloy et al. 2010. Mol Gen Metabol 99:72-79. |
| H305Q | Ligand binding | Malloy et al. 1997 J Clin Invest 99:297-304. |
| R391C | RXR binding | Whitfield et al. 1996 Mol Endocrinol 10:1617-1631. |
| E420K | Coactivator binding | Malloy et al. 2002 Mol Endocrinol 16:2538-2546. |
| Y295X | Truncated protein, proximal | Malloy et al. 1990 J Clin Invest 86:2071-2079. |
| Y401X | Truncated protein, distal | Malloy et al. 2007 Arch Biochem Biophys 460:285-292. |
| H305Q/ BSCL2 (DM) | VDR: Ligand binding BDCL2: Truncated protein | Malloy et al. 1997 J Clin Invest 99:297-304. |

(The V26M mutation is in the VDR DNA-binding domain (DBD) and affects interactions with DNA and inhibits VDR transactivation. The V26M mutation does not affect 1,25(OH)$_2$D$_3$ binding or interactions with RXR or coactivators. The H305Q mutation is in the VDR ligand-binding domain (LBD) and alters the contact point for the 25-hydroxyl group of 1,25(OH)$_2$D$_3$ and reduces VDR's affinity for 1,25(OH)$_2$D$_3$. The R391C mutation reduces RXR binding and inhibits VDR transactivation. The E420K mutation abolishes coactivator binding to the AF-2 domain in the LBD and inhibits VDR transactivation. The E420K mutation does not affect 1,25(OH)$_2$D$_3$ binding, DNA binding or RXR heterodimerization. The Y295X and Y401X mutations introduce a premature stop signals that truncate the VDR. The VDR Y295X truncated protein is not expressed due to nonsense-mediated mRNA decay. The VDR Y401X truncated protein is expressed and is able to heterodimerize with RXR and bind to DNA but lacks 1,25(OH)$_2$D$_3$ binding.) The patient with the Y401X mutation does not have alopecia indicating that this mutant VDR maintains some functional activity. The H305Q/BSCL2 double mutant (DM) has homozygous mutations in the VDR (H305Q) and BSCL2 (1016/-3C to G) genes.

Human dermal fibroblasts have been shown to develop features of adipocytes when induced with an adipogenic cocktail (Junker (2010) Cells Tissue Organ. 191:105-118). Therefore, we treated the fibroblasts with an adipogenic cocktail (dexamethasone, insulin, IBMX (DIM)) alone or in combination with the PPARγ agonist rosiglitazone (DIMR). Microscopic examination revealed many visible fat droplets within 5-6 days in the HVDRR fibroblasts cells treated with DIMR. At day 14, the HVDRR cells treated with DIMR contained many cells with intracellular droplets (FIG. 1, A and B). Treatment with DIM alone also induced lipid droplet formation in the HVDRR cells but to a lesser degree. When compared to the HVDRR cells, the normal control cells exhibited fewer oil red O (which binds neutral lipids) staining positive cells after treatment with DIM or DIMR (FIG. 1A). We also examined adipogenesis in fibroblasts from a patient with homozygous mutations in both the VDR (H305Q) and BSCL2 genes compared to a sibling with only the VDR (H305Q) mutation. The BSCL2 mutation in intron 6 (1016/-3C to G) causes exon 7 to be skipped and results in a frameshift and premature stop codon (Van Maldergem (1996) Am. J. Med. Genet. 64:506-513). Mutations in BSCL2 cause Berardinelli-Seip congenital lipodystrophy (Magre (2001) Nat. Genet. 28:365-370). BSCL2 is a membrane protein located in the endoplasmic reticulum and is thought to be involved lipid droplet formation (Chen (2012) Mol. Cell Biol. 32:1099-1111). The cells with the VDR/BSCL2 mutations had very few lipid droplets after treatment with DIMR confirming a role for BSCL2 in droplet formation. At day 14, none of the HVDRR cells or normal control cells treated with vehicle without DIM (FIG. 1A, top row) or rosiglitazone alone had visible droplets and were negative for oil red O staining.

Having successfully differentiated the WT and mutant fibroblasts into what histologically appeared to be adipocyte-like cells, we next analyzed the expression of the adipocyte markers PPARγ and FABP4. These transcripts are highly expressed in both brown and white adipocytes and co-induction of expression of these markers indicate an adipocyte specific expression profile in the cells (Cristancho (2011) Nat. Rev. Mol. Cell Biol. 12:722-734). Gene expression studies showed that WT control and HVDRR cells expressed similar levels of the pan-adipocyte markers PPARγ and FABP4 (FIG. 1 C-F). PPARγ expression was low in the undifferentiated WT control cells but was upregulated by ~5-fold after treatment with DIM alone. The HVDRR cells expressed similar levels of PPARγ mRNA after DIM treatment (FIG. 1C). DIMR treatment further induced PPARγ expression ~10-fold in the WT control cells and ~20-fold in the HVDRR cells (FIG. 1D). FABP4 expression was undetectable in the undifferentiated cells but was significantly upregulated in the WT control and HVDRR cells when differentiated with DIM alone (FIG. 1E). FABP4 was highly upregulated in several HVDRR cells (R391C, E420K and Y401X) after DIM treatment and further increased in both the WT control and HVDRR cells differentiated with DIMR. (FIG. 1, E and F). Interestingly, the VDR/BSCL2 double mutant (DM) expressed significantly lower levels of PPARγ and FABP4 when treated with DIM or DIMR even when compared to the sibling with the same VDR mutation but no BSCL2 mutation; confirming earlier reports of a role for BSCL2 in adipogenesis (Payne (2008) Diabetes. 57:2055-2060) and indicating that this BSCL2 activity is upstream of VDR (FIG. 1, C-F). Together, our results demonstrate that the DIM differentiated WT control and HVDRR cells exhibit an expression profile signature of adipocytes.

To investigate the functional capabilities of the differentiated human fibroblasts, we examined their ability to carry out lipolysis, by measuring the release of glycerol after exposure to the synthetic catecholamine β-adrenergic agonist isoproterenol. In these assays the WT control cells showed a 2.5-fold increase in glycerol release while the HVDRR cells exhibited a 1.5-4-fold increase in glycerol release compared to the undifferentiated cells (FIG. 1G). Of note, the H305Q/BSCL2 double mutant had significantly less induction of lipolysis compared to the H305Q single mutant, indicating that the level of lipolysis reports successful differentiation. Together, these results demonstrate that both the WT control and HVDRR differentiated cells exhibit functional properties of adipocytes.

Cell Autonomous and Ligand Independent Regulation of UCP1 by VDR. Studies have shown that the white adipose tissue from VDRKO mice has features of brown fat including small lipid droplets and expression of UCP1, a phenotype that has been referred to as 'beige' fat (Ishibashi (2010) Science. 328:1113-1114). However, the mechanism regulating this finding had not been elucidated and the relevance for humans was unknown. Therefore, to determine if HVDRR cells autonomously regulate the beiging process, we examined the expression of UCP1 in differentiated WT control and HVDRR human cells. Neither WT nor HVDRR cells expressed UCP1 prior to differentiation.

Figure 2:
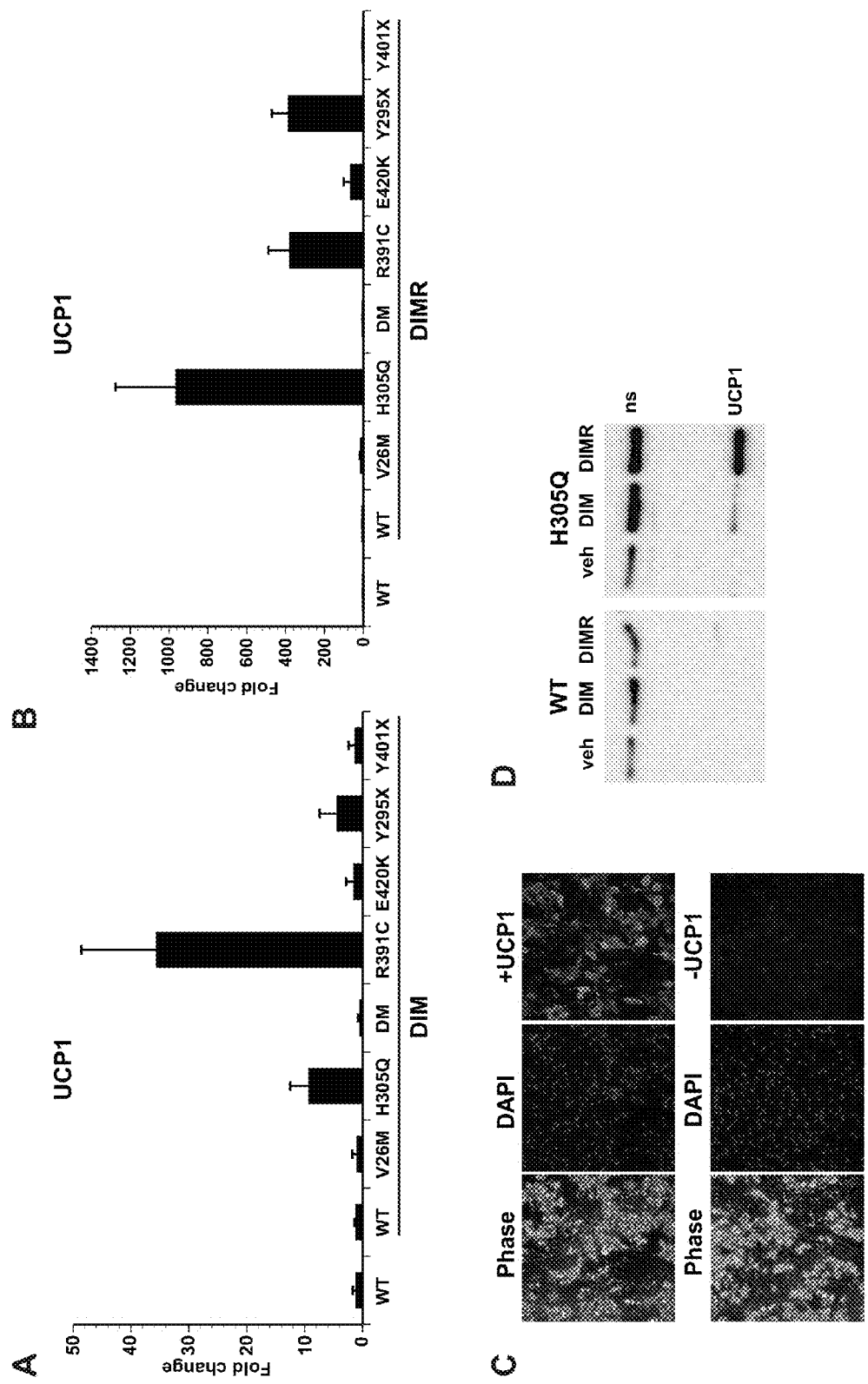
FIG. 2. Differentiated human HVDRR fibroblasts express the brown fat marker UCP1. Relative gene expression of UCP1 in WT and HVDRR cells treated with DIM (A) or DIMR (B) compared to vehicle control. Three independent experiments were performed. Error bars are s.d.'s. (C) HVDRR (H305Q) fibroblasts were differentiated with DIMR for 14 days and labelled with DAPI (blue) or stained with antibodies against UCP1 (green). The left panels show corresponding phase contrast image. (D) Immunoblots of UCP1 in WT control cells and in HVDRR cells with H305Q mutation following treatment with vehicle, DIM or DIMR. Non-specific band (ns).

We discovered that UCP1 was upregulated 9-fold in H305Q, 35-fold in R391C, and 4-fold in Y295X HVDRR cells after DIM treatment (FIG. 2A). On the other hand, UCP1 was undetectable in the WT control cells and the HVDRR cells with the V26M, E420K and Y401X mutations after DIM treatment. The addition of rosiglitazone to the DIM induction (DIMR) further stimulated UCP1 levels dramatically in specific HVDRR cells (960-fold in H305Q, 375-fold in R391C, and 383-fold in Y295X). Of note, compared to these mutant HVDRR cells, the levels of UCP1 expression after DIMR treatment remained significantly lower in the WT (5-fold) and the other HVDRR cells (11-fold in V26M, 62-fold in E420K and 4-fold in Y401 X). In the VDR/BSCL2 double mutant (DM), UCP1 was undetectable after DIM treatment but was stimulated 4-fold after treatment with DIMR (FIG. 2B). While significantly lower than in the H305Q, R391C and Y295X HVDRR cells, the detectable levels of UCP1 expression in WT and V26M, E420K and Y401X HVDRR cells after DIMR treatment may have been induced by rosiglitazone, as chronic exposure to PPARγ agonists induces UCP1 expression in white adipocyte cultures (Petrovic (2010) J. Biol. Chem. 285:7153-7164). Importantly, the very strong induction in the H305Q, R391C and Y295X HVDRR cells, suggests that VDR regulates a distinct, and cell autonomous, mechanism for modulating UCP1 expression.

The data from the HVDRR cells demonstrate that UCP1 expression is negatively regulated by the VDR in human cells. The high level of UCP1 in the R391C mutant indicates that RXR binding is necessary for this inhibitory action of the VDR as this mutant has otherwise intact VDR protein (Whitfield (1996) Mol. Endocrinol. 10:1617-1631). Of note, the HVDRR cells with the E420K mutation (located in the activation function 2 (AF2) domain) and Y401X mutation (that deletes the AF2 domain) are defective in binding coactivators (e.g., DRIP205, SRC1) (Malloy (2007) Arch Biochem. Biophys. 460:285-292) (Nakajima (1994) Mol. Endocrinol. 8:159-172). Both of these mutant cells express UCP1 at levels similar to the WT control, indicating that coactivator interaction is not required for the inhibitory activity of the VDR on UCP1 expression. In addition, the Y401X mutant does not bind calcitriol (Malloy (2007) Arch Biochem. Biophys. 460: 285-292), supporting a role of an unliganded activity of the VDR in regulating UCP1. In the V26M mutant (with an amino acid change in the first zinc finger of the DNA-binding domain (DBD)), the levels of UCP1 are also similar to the WT control. This finding supports prior studies suggesting that the first zinc finger in VDR DBD is not required for repression activity (Kim (2007) Mol. Endocrinol. 21:334-342). Unexpectedly, the cells with the H305Q mutation (with lower affinity for calcitriol from disrupting the contact point for the 25-hydroxyl group of calcitriol (Malloy (1997) J. Clin. Invest. 99:297-304) (Roche) (2010) J. Steroid Biochem. Mol. Biol. 121:84-87)) have significantly elevated UCP1 levels. The findings in the H305Q and Y401X mutants further demonstrate that the repressive action of the WT VDR on UCP1 expression occurs independently from ligand binding. Moreover, these results indicate that H305 is a critical amino acid involved in unliganded VDR actions and reveal a previously unknown function of this amino acid.

To determine if UCP1 protein is expressed in the mutant cells we performed immunohistochemistry on the differentiated HVDRR cells using a UCP1 antibody. After 14 days, the HVDRR (H305Q) cells generally had a multilocular lipid droplet morphology, a feature of brown adipocytes, as shown in the phase contrast images (FIG. 2C). Strong UCP1 staining was observed in the cytoplasm of the lipid droplet containing cells, compared with almost undetectable levels in the undifferentiated cells. No staining was observed in the HVDRR cells without the UCP1 antibody (FIG. 2C). Immunoblotting confirmed that UCP1 was not expressed in undifferentiated (vehicle treated) WT control or HVDRR cells. HVDRR cells that expressed UCP1 RNA after differentiation, also had detectable UCP1 protein following DIM treatment that was further induced with DIMR. In the WT control cells, UCP1 was undetectable in DIM or DIMR samples (FIG. 2D).

Figure 3:
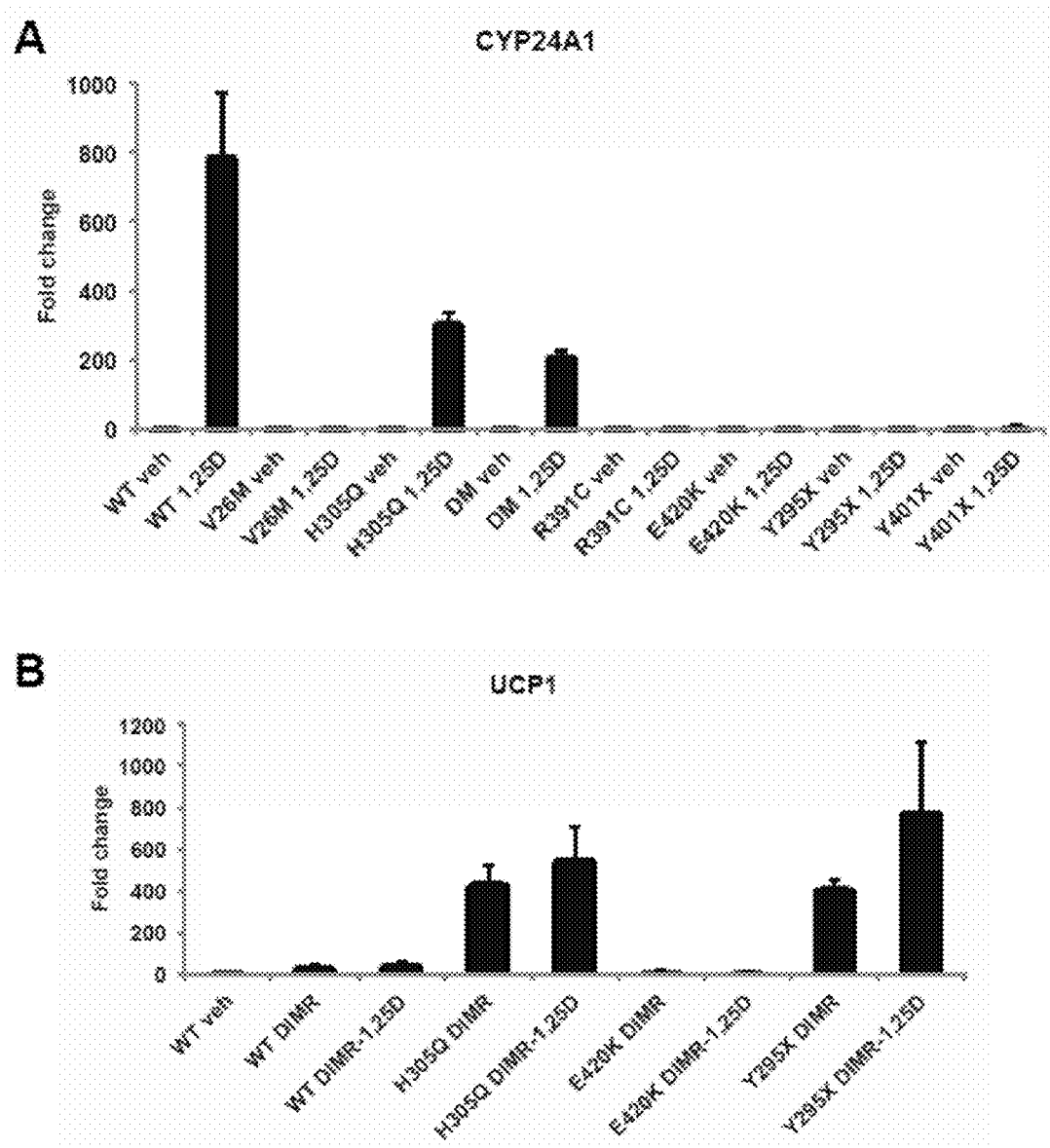
FIG. 3. HVDRR mutant fibroblasts exhibit resistance to calcitriol. (A) Control and HVDRR fibroblasts were treated with vehicle (0.1% ethanol) or 10 nM calcitriol for 6 hr. RT-qPCR assays were carried out for CYP24A1 a marker of calcitriol responsiveness. DM denotes double mutant with H305Q mutation in the VDR and BSCL2 mutation. (B) Pharmacologic doses of calcitriol do not alter UCP1 levels in differentiated HVDRR cells. Relative gene expression of UCP1 in WT and HVDRR fibroblasts differentiated with DIMR or DIMR plus 10 nM calcitriol for 14 days.

It is important to highlight that the studies described above were done without the addition of calcitriol and there is no induction of 24-hydroxylase (CYP24A1), the classic VDR target gene, unless calcitriol is added to the cultures (FIG. 3A). Together our results indicate that regulation of UCP1 expression by VDR occurs ligand independently. Since the ligand binding affinity of the H305Q mutant is reduced but adding excess calcitriol (10 nM) rescues the induction of 24-hydroxylase expression by VDR ex vivo (FIG. 3A) and can be used to treat the rickets that develops in patients with this mutation (Malloy (1997) J. Clin. Invest. 99:297-304), cells with this mutation provide an opportunity to further test the role of ligand in the regulation of UCP1. Therefore, we tested if the addition of vitamin D would rescue the repression of UCP1 expression by VDR. We found that even pharmacologic doses of vitamin D did not significantly alter UCP1 levels in the H305Q or any of the other mutants compared to the absence of ligand (FIG. 3B). These results confirm that the regulation of UCP1 can be uncoupled from other VDR activities and is ligand independent.

Figure 4:
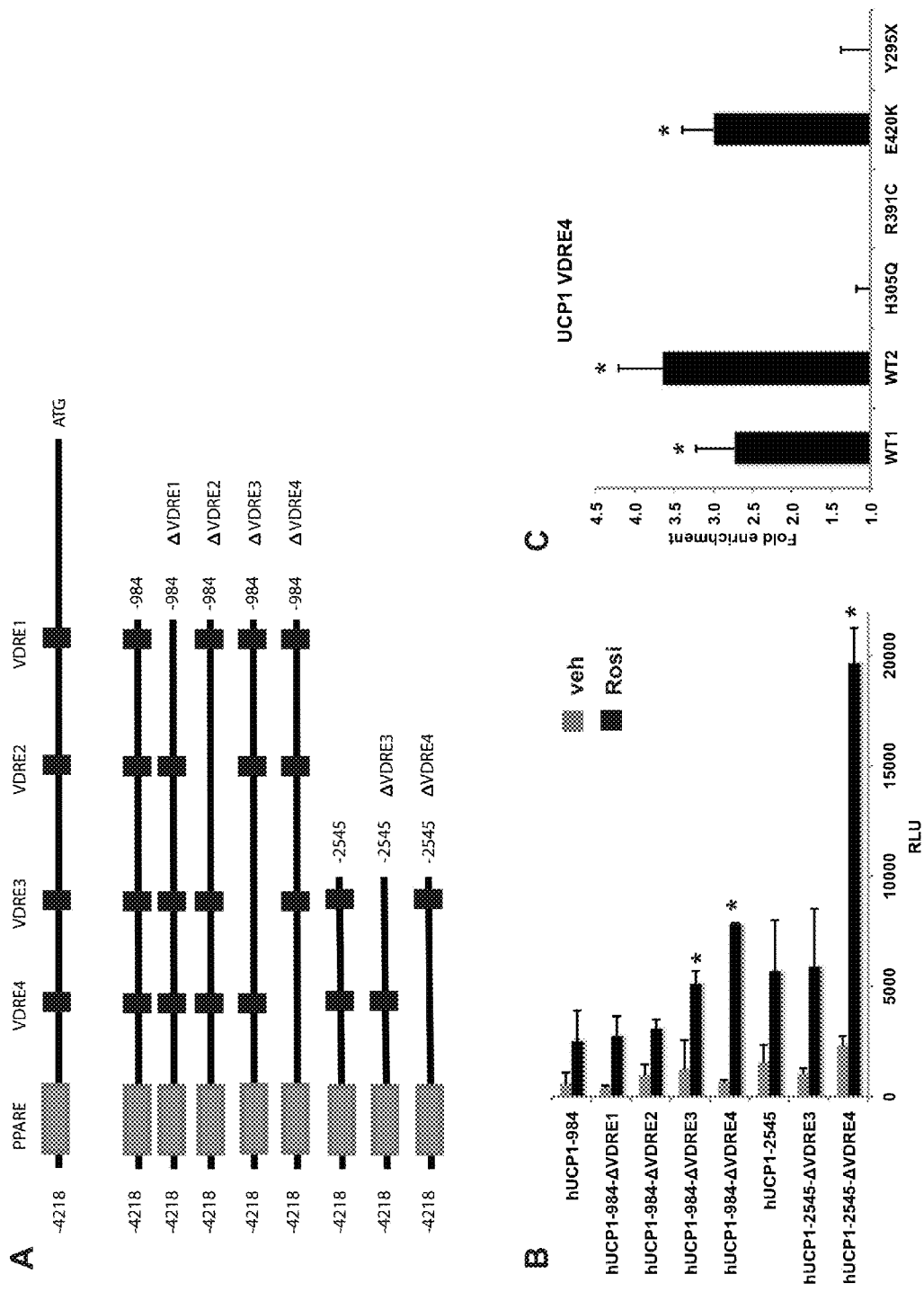
FIG. 4. A VDRE in the human UCP1 upstream sequence negatively regulates UCP1. (A) In silico analyses and scanning ChIP analyses identified 4 potential VDR binding sites in the region from +1 to −4218 of the UCP1 upstream sequence (VDREs1-4). Deletions of the VDREs were generated by PCR and analyzed by reporter assays. (B) COS-7 cells were transiently co-transfected with the different deletion constructs with VDR, RXR and PPARγ expression plasmids. Cells were treated with DMSO (veh) or 1 μM rosiglitazone (Rosi) for 48 hrs then assayed for luciferase activity. (C) ChIP analyses of VDR binding to the endogenous UCP1 VDRE4 in WT and HVDRR mutants. Error bars represent s.d.'s from three independent experiments. * p<0.005.

VDR Directly Regulates UCP1 Expression in Human Cells. Previous studies of the human UCP1 upstream sequence identified an enhancer region, between −4218 bp to −3698 bp relative to the translational start site, that contains binding sites for PPARγ (del Mar Gonzalez-Barroso (2000) J. Biol. Chem. 275:31722-31732) (Oberkofler (2002) J. Biol. Chem. 277:16750-16757). Using a combination of in silico analyses and ChIP scanning we identified four potential vitamin D response elements between −3698 bp to −984 bp in the sequence upstream of the translational start site of the human UCP1 gene. To explore the mechanisms underlying VDR-mediated repression of UCP1, we generated two constructs containing the PPARγ enhancer and all 4 putative VDREs (−4218 to −984 bp; VDRE1-4) or 2 VDREs (−4218 to −2545 bp; VDRE3-4) upstream of a luciferase reporter gene (FIG. 4A). We then generated deletions of each VDRE and tested their effects on rosiglitazone-induced transactivation by PPARγ. These experiments were performed in the absence of calcitriol. As shown in FIG. 4B, rosiglitazone induced luciferase activity of the −4218 to −984 construct containing all 4 VDREs. Deletion of VDRE1 and VDRE2 had no effect on this activity. Deletion of VDRE3 resulted in a modest increase in activity while deletion of VDRE4 resulted in a doubling of the rosiglitazone induced reporter activity compared to the parent construct containing all 4 VDREs. The −4218 to −2545 bp construct had ~2-fold higher levels of rosiglitazone induced activity compared to the longer −4218 to −984 bp construct. Deletion of VDRE3 had no effect on this activity. Deletion of VDRE4, however, resulted in a strong stimulation by rosiglitazone that was ~4-fold greater than the intact −4218 to −2545 bp construct and ~10-fold higher than the intact −4218 to −984 bp construct (FIG. 4B). These results demonstrate that VDRE4 is a critical negative regulatory element controlling UCP1 expression.

We then used ChIP assays and qPCR to analyze endogenous occupancy of VDRE4 by VDR in intact human WT and HVDRR cells. We found that the WT VDR and the E420K mutant VDR were competent to occupy VDRE4 (FIG. 4C). Importantly, the H305Q, R391C and Y295X mutants all failed to occupy VDRE4 (FIG. 4C). These results reveal a scenario in which unliganded VDR mediated repression of UCP1 is achieved by WT and mutant VDRs capable of occupancy of the VDRE4 regulatory element. The fact that the H305Q mutant was unable to repress UCP1 and failed to occupy VDRE4 suggests that H305 is a critical amino acid involved in the unliganded actions of the VDR and reveals a previously unknown function of this amino acid in addition to its known function as a contact point for the 25-hydroxyl group in $1,25(OH)_2D_3$.

```
Reference sequence of Human VDR wild-type,
                                    SEQ ID NO: 1
MEAMAASTSL PDPGDFDRNV PRICGVCGDR ATGFHFNAMT

CEGCKGFFRR SMKRKALFTC PFNGDCRITK DNRRHCQACR

LKRCVDIGMM KEFILTDEEV QRKREMILKR KEEEALKDSL

RPKLSEEQQR IIAILLDAHH KTYDPTYSDF CQFRPPVRVN

DGGGSHPSRP NSRHTPSFSG DSSSSCSDHC ITSSDMMDSS

SFSNLDLSEE DSDDPSVTLE LSQLSMLPHL ADLVSYSIQK

VIGFAKMIPG FRDLTSEDQI VLLKSSAIEV IMLRSNESFT

MDDMSWTCGN QDYKYRVSDV TKAGHSLELI EPLIKFQVGL

KKLNLHEEEH VLLMAICIVS PDRPGVQDAA LIEAIQDRLS

NTLQTYIRCR HPPPGSHLLY AKMIQKLADL RSLNEEHSKQ

YRCLSFQPEC SMKLTPLVLE VFGNEIS
```

Discussion

The control of energy metabolism in humans is a complex and carefully regulated process. Understanding how energy utilization is regulated at the molecular level has broad medical implications. In particular, the rise in prevalence of obesity and metabolic disease in the population underscores the need to advance our understanding of this process in order to develop better therapeutic options for these patients.

Brown fat, once thought to fully regress in humans after the neonatal period, has now been convincingly identified throughout adult life (Cypess (2009) N. Engl. J. Med. 360: 1509-1517) (Ouellet (2012) J. Clin. Invest. 122:545-552). As brown fat is especially successful at burning energy, increasing the levels or the features of brown fat in cells has emerged as an attractive potential strategy for treating patients with excess energy stores. As opposed to rodents, it appears that the majority of brown fat cells in adult humans have a molecular signature of beige cells (Sharp (2012) PLoS ONE. 7:e49452) (Wu (2012) Cell. 150:366-376). It is therefore reasonable to speculate that most physiologically relevant human brown fat in adults is analogous to the beige fat identified in rodent models.

Inspired by studies of mouse models that revealed that altering VDR levels modulates the levels of brown fat features in white adipose depots (Narvaez (2009) Endocrinology 150: 651-661) (Narvaez (2009) Endocrinology 150:651-661), we speculated that VDR could regulate features of beiging in human cells. Further, we hypothesized that studies utilizing our collection of cells isolated from patients with HVDRR, that contain various naturally occurring mutations in VDR, would help us to resolve whether the connection between VDR and beiging was cell autonomous as well as define the specific mechanism. Our results indicate that unliganded VDR can directly regulate the critical functional mediator of energy consumption, UCP1, by binding to a VDRE in the promoter proximal region of the gene and inhibiting expression. We show that changes in UCP1 levels can occur cell autonomously, rather than requiring the recruitment of a distinct cell lineage. When VDR is deleted or mutated in a way that disrupts occupancy of a specific VDRE, UCP1 is derepressed and expressed. Therefore, our data suggest a paradigm where VDR modulates beige versus white adipocyte identity as opposed to a toggle in the recruitment of distinct progenitor cell populations. These results will have important implications for human health, including a therapeutic strategy of developing factors that specifically target releasing the beige fat expression profile of human cells.

Materials and Methods

Cell culture. Isolation of these dermal skin fibroblasts from normal and HVDRR patients has been previously described (Table I). Cells were grown in DMEM containing 4.5 g glucose, 10 mM sodium pyruvate and 10% fetal bovine serum (FBS) at 37° C. in an atmosphere of 5% CO2/95% air.

Differentiation of human fibroblasts. Cells were seeded in six well plates in DMEM, 10% FBS and grown to confluence. Cells were then treated with either vehicle (0.1% ethanol, 0.1% DMSO), 1 μM dexamethasone, 0.5 mM isobutyl-methylxanthine (IBMX), 10 μM insulin (DIM) or DIM plus 1 μM rosiglitazone (DIMR). Cells were treated for 10-14 days.

Oil red O staining. After differentiation the cells were washed twice with 1× phosphate buffered-saline (PBS) and then fixed in 10% formaldehyde in 1×PBS for 60 min. Cells were washed twice with water and stained with oil red O for 50 min at room temperature. The cells were washed three times with water.

Real-time RT-PCR. Fibroblasts were treated for 20 hr with vehicle (0.1% ethanol), 1 mM rosiglitazone, or DIM plus 1 mM rosiglitazone in DMEM containing 10% FBS. RNA was isolated using RNeasy Plus Mini Kit (Qiagen, Valencia, Calif.). cDNA was prepared using Maxima Universal First Strand cDNA Synthesis kit (Fisher Scientific, Pittsburgh, Pa.). Real time PCR was performed using the DyNAmo ColorFlash qPCR kit (Fisher Scientific). Relative changes in mRNA expression were assessed by the 2-ΔΔC(T) method and normalized to that of the reference gene glyceraldehyde phosphate dehydrogenase (GAPDH). The values from vehicle treated normal control fibroblasts were set at 1. Assays were performed in triplicate. The primers used are listed in Table II.

TABLE II

| QPCR primers | | |
| --- | --- | --- |
| Gene | Upper Primer (5'-3') | Lower Primer (5'-3') |
| CYP24A1 | GGCTCTTTGTTGGATTGTCC | AAACCAGCAGTGAACCCTGT |
| PPARG | GCAGGAGATCTACAAGGACTTG | CCCTCAGAATAGTGCCTGG |
| FABP4 | GGGGTGTCCTGGTACATGTGCA | TCATGACGCATTCCACCACCAGT |
| UCP1 | TCGGACGTACACCCGACCCTG | TTCACCTTGGACCTGGAGCCG |
| GAPDH | GAAGGTGAAGGTCGGAGTCA | GATCTCGCTCCTGGAAGATG |
| (from top to bottom then left to right SEQ ID NOs: 2-11) | | |

| Primers used in cloning UCP1 upstream sequence | |
| --- | --- |
| Name | Sequence (5'-3') |
| hUCP1pro +83-L | CCTTCTCGAGTCCGCCAAGCACGCCGCTATTCC |
| hUCP1pro -984-L | CCTTCTCGAGCTTGGCTCCAGGTCAGCTC |
| hUCP1pro -2545-L | CCTTCTCGAGGAGGCTGATGGCTAAGCAGT |
| hUCP1pro -4218-U | CAGGTACCTAACAGGGTATTTCCCAG |
| (from top to bottom SEQ ID NOs: 12-15) | |

| Primers used in deleting VDREs in UCP1 upstream sequence | |
| --- | --- |
| Name | Sequence (5'-3') |
| hUCP1-delVDRE1 | AGTACAGATGACTTTAGCTGGAGAGCTGCACCT |
| hUCP1-delVDRE1-r | AGGTGCAGCTCTCCAGCTAAAGTCATCTGTACT |
| hUCP1-delVDRE2 | TACAGCCTCATCCCTCTCTCTTTCTTCCCC |
| hUCP1-delVDRE2-r | GGGGAAGAAAGAGAGAGGGATGAGGCTGTA |
| hUCP1-delVDRE3 | ACCTGTTGATAGCAGAACAAGGAATAAGGTCT |

TABLE II-continued

QPCR primers

| | |
|---|---|
| hUCP1-delVDRE3-r | AGACCTTATTCCTTGTTCTGCTATCAACAGGT |
| hUCP1-delVDRE4 | GGATCAGGAATTTAGCTTCTGCTTTACTGA |
| hUCP1-delVDRE4-r | TCAGTAAAGCAGAAGCTAAATTCCTGATCC |

(from top to bottom SEQ ID NOs: 16-23)

ChIP primers

| Name | Sequence (5'-3') |
|---|---|
| hUCP1-VDRE4-U | TCTCACAATTTTATGGATCAGGAA |
| hUCP1-VDRE4-L | CACCAGGCACCAGAGTACAG |

(from top to bottom SEQ ID NOs: 24-25)

Lipolysis assay. To measure lipolysis activity, control and differentiated fibroblasts, were starved in DMEM containing 1% FBS overnight. Cells were then incubated for 24 hrs in HBSS (Hank's balanced salt solution) containing 2% fatty-acid-free BSA and 10 µM isoproterenol. The culture medium was collected for glycerol measurement using the free glycerol reagent (Sigma, St. Louis, Mo.).

Reporter constructs and assay. DNA fragments of sequence upstream of the human UCP1 MET translational start site were amplified by PCR from human genomic DNA and cloned into pGL3-basic or pGL4.1 TATA luciferase reporter vectors (Promega, Madison Wis.). Deletions of putative VDREs were generated by PCR using Pfu polymerase (Stratagene, La Jolla, Calif.). The primers used for cloning and mutagenesis are listed in Supplemental Table 1. The reporter plasmids were transiently co-transfected with VDR, RXRα and PPARγ expression vectors in COS-7 cells using Polyfect (Qiagen). Cells were then treated with 1 µM rosiglitazone. Forty-eight hours later, cells were collected and reporter gene assays were carried out using the Dual Luciferase System (Promega, Madison).

ChIP Assay. Human fibroblasts grown to confluence were fixed in 1% formaldehyde for 10 min. Cells were sonicated in a Bioruptor (Diagenode Inc., Denville, N.J.). Samples were precipitated with anti-VDR C-20 antibody (Santa Cruz Biotechnology, Santa Cruz, Calif.) or normal rabbit IgG. Immunoprecipitates were collected using ChIP Grade Protein G Magnetic Beads (Cell Signaling, Danvers, Mass.). Real time PCR was performed using the DyNAmo ColorFlash qPCR kit and primers listed in Table II above.

Statistics. All experiments were performed with biological triplicates. Error bars represent standard deviations from the mean. Student t-tests were used for pairwise comparisons and $P<0.05$ was considered significant.

Study Approval. Informed consent was obtained from the patients and parents under a Stanford University IRB approved protocol.

---

What is claimed is:

1. A method of screening for an antagonist agent that enhances human brown or beige fat adipogenesis mediated by unliganded vitamin D receptor (VDR) activity, the method comprising:
   combining a candidate agent with a vitamin D receptor present in an intact human cell capable of adipogenesis and selected from a pre-adipocyte, an adipocyte progenitor, an adipocyte stem cell and a fibroblast; and
   determining inhibition of unliganded VDR activity by differentiation of cells under adipogenic conditions to brown, beige or white adipocyte phenotypes in the absence or presence of a candidate agent;
   wherein brown or beige fat adipogenesis is enhanced by interfering with unliganded VDR repression of UCP1 expression.

2. The method of claim 1 wherein the activity is occupancy of a vitamin D response element (VDRE).

3. The method of claim 1 wherein the unliganded vitamin D receptor (VDR) activity includes inhibiting VDR occupancy of a vitamin D response element (VDRE) in the absence of vitamin D or an analog thereof.

4. The method of claim 2, wherein the VDRE is VDRE4 of UCP1.

5. A method of screening for an antagonist agent that enhances human brown or beige fat adipogenesis mediated by unliganded vitamin D receptor (VDR) activity, the method comprising:
   contacting a candidate agent with a DNA comprising vitamin D response element 4 (VDRE4) in the absence of vitamin D or an analog thereof and determining if the agent occupies VDRE4 or inhibits VDR occupancy of VDRE4, and further testing the agent by the method comprising:
   combining the agent with a human adipocyte or pre-adipocyte cultured in the presence of an adipogenic cocktail; and
   determining inhibition of unliganded VDR activity by differentiation of cells under adipogenic conditions to brown, beige or white adipocyte phenotypes in the absence or presence of the candidate agent;
   wherein brown or beige fat adipogenesis or adipocyte activity is enhanced by interfering with unliganded VDR repression of UCP1 expression.

\* \* \* \* \*

SEQUENCE LISTING

```
<160> NUMBER OF SEQ ID NOS: 25

<210> SEQ ID NO 1
<211> LENGTH: 427
<212> TYPE: PRT
<213> ORGANISM: Homo sapiens

<400> SEQUENCE: 1

Met Glu Ala Met Ala Ala Ser Thr Ser Leu Pro Asp Pro Gly Asp Phe
1               5                   10                  15

Asp Arg Asn Val Pro Arg Ile Cys Gly Val Cys Gly Asp Arg Ala Thr
                20                  25                  30

Gly Phe His Phe Asn Ala Met Thr Cys Glu Gly Cys Lys Gly Phe Phe
            35                  40                  45

Arg Arg Ser Met Lys Arg Lys Ala Leu Phe Thr Cys Pro Phe Asn Gly
        50                  55                  60

Asp Cys Arg Ile Thr Lys Asp Asn Arg Arg His Cys Gln Ala Cys Arg
65                  70                  75                  80

Leu Lys Arg Cys Val Asp Ile Gly Met Met Lys Glu Phe Ile Leu Thr
                85                  90                  95

Asp Glu Glu Val Gln Arg Lys Arg Glu Met Ile Leu Lys Arg Lys Glu
                100                 105                 110

Glu Glu Ala Leu Lys Asp Ser Leu Arg Pro Lys Leu Ser Glu Glu Gln
            115                 120                 125

Gln Arg Ile Ile Ala Ile Leu Leu Asp Ala His His Lys Thr Tyr Asp
        130                 135                 140

Pro Thr Tyr Ser Asp Phe Cys Gln Phe Arg Pro Pro Val Arg Val Asn
145                 150                 155                 160

Asp Gly Gly Gly Ser His Pro Ser Arg Pro Asn Ser Arg His Thr Pro
                165                 170                 175

Ser Phe Ser Gly Asp Ser Ser Ser Ser Cys Ser Asp His Cys Ile Thr
            180                 185                 190
```

```
Ser Ser Asp Met Met Asp Ser Ser Phe Ser Asn Leu Asp Leu Ser
        195                 200                 205

Glu Glu Asp Ser Asp Asp Pro Ser Val Thr Leu Glu Leu Ser Gln Leu
    210                 215                 220

Ser Met Leu Pro His Leu Ala Asp Leu Val Ser Tyr Ser Ile Gln Lys
225                 230                 235                 240

Val Ile Gly Phe Ala Lys Met Ile Pro Gly Phe Arg Asp Leu Thr Ser
                245                 250                 255

Glu Asp Gln Ile Val Leu Leu Lys Ser Ser Ala Ile Glu Val Ile Met
            260                 265                 270

Leu Arg Ser Asn Glu Ser Phe Thr Met Asp Asp Met Ser Trp Thr Cys
        275                 280                 285

Gly Asn Gln Asp Tyr Lys Tyr Arg Val Ser Asp Val Thr Lys Ala Gly
    290                 295                 300

His Ser Leu Glu Leu Ile Glu Pro Leu Ile Lys Phe Gln Val Gly Leu
305                 310                 315                 320

Lys Lys Leu Asn Leu His Glu Glu Glu His Val Leu Leu Met Ala Ile
                325                 330                 335

Cys Ile Val Ser Pro Asp Arg Pro Gly Val Gln Asp Ala Ala Leu Ile
            340                 345                 350

Glu Ala Ile Gln Asp Arg Leu Ser Asn Thr Leu Gln Thr Tyr Ile Arg
        355                 360                 365

Cys Arg His Pro Pro Gly Ser His Leu Leu Tyr Ala Lys Met Ile
    370                 375                 380

Gln Lys Leu Ala Asp Leu Arg Ser Leu Asn Glu Glu His Ser Lys Gln
385                 390                 395                 400

Tyr Arg Cys Leu Ser Phe Gln Pro Glu Cys Ser Met Lys Leu Thr Pro
                405                 410                 415

Leu Val Leu Glu Val Phe Gly Asn Glu Ile Ser
            420                 425

<210> SEQ ID NO 2
<211> LENGTH: 20
<212> TYPE: DNA
<213> ORGANISM: Artificial Sequence
<220> FEATURE:
<223> OTHER INFORMATION: synthetic polynucelotide

<400> SEQUENCE: 2
ggctctttgt tggattgtcc                                                   20

<210> SEQ ID NO 3
<211> LENGTH: 22
<212> TYPE: DNA
<213> ORGANISM: Artificial Sequence
<220> FEATURE:
<223> OTHER INFORMATION: synthetic polynucelotide

<400> SEQUENCE: 3
gcaggagatc tacaaggact tg                                                22

<210> SEQ ID NO 4
<211> LENGTH: 22
<212> TYPE: DNA
<213> ORGANISM: Artificial Sequence
<220> FEATURE:
<223> OTHER INFORMATION: synthetic polynucelotide

<400> SEQUENCE: 4
```
ggggtgtcct ggtacatgtg ca                              22

<210> SEQ ID NO 5
<211> LENGTH: 21
<212> TYPE: DNA
<213> ORGANISM: Artificial Sequence
<220> FEATURE:
<223> OTHER INFORMATION: synthetic polynucelotide

<400> SEQUENCE: 5
tcggacgtac acccgaccct g                               21

<210> SEQ ID NO 6
<211> LENGTH: 20
<212> TYPE: DNA
<213> ORGANISM: Artificial Sequence
<220> FEATURE:
<223> OTHER INFORMATION: synthetic polynucelotide

<400> SEQUENCE: 6
gaaggtgaag gtcggagtca                                 20

<210> SEQ ID NO 7
<211> LENGTH: 20
<212> TYPE: DNA
<213> ORGANISM: Artificial Sequence
<220> FEATURE:
<223> OTHER INFORMATION: synthetic polynucelotide

<400> SEQUENCE: 7
aaaccagcag tgaaccctgt                                 20

<210> SEQ ID NO 8
<211> LENGTH: 19
<212> TYPE: DNA
<213> ORGANISM: Artificial Sequence
<220> FEATURE:
<223> OTHER INFORMATION: synthetic polynucelotide

<400> SEQUENCE: 8
ccctcagaat agtgcctgg                                  19

<210> SEQ ID NO 9
<211> LENGTH: 23
<212> TYPE: DNA
<213> ORGANISM: Artificial Sequence
<220> FEATURE:
<223> OTHER INFORMATION: synthetic polynucelotide

<400> SEQUENCE: 9
tcatgacgca ttccaccacc agt                             23

<210> SEQ ID NO 10
<211> LENGTH: 21
<212> TYPE: DNA
<213> ORGANISM: Artificial Sequence
<220> FEATURE:
<223> OTHER INFORMATION: synthetic polynucelotide

<400> SEQUENCE: 10
ttcaccttgg acctggagcc g                               21

<210> SEQ ID NO 11
<211> LENGTH: 20
<212> TYPE: DNA
<213> ORGANISM: Artificial Sequence
<220> FEATURE:
<223> OTHER INFORMATION: synthetic polynucelotide

<400> SEQUENCE: 11
gatctcgctc ctggaagatg             20

<210> SEQ ID NO 12
<211> LENGTH: 33
<212> TYPE: DNA
<213> ORGANISM: Artificial Sequence
<220> FEATURE:
<223> OTHER INFORMATION: synthetic polynucelotide

<400> SEQUENCE: 12
ccttctcgag tccgccaagc acgccgctat tcc             33

<210> SEQ ID NO 13
<211> LENGTH: 29
<212> TYPE: DNA
<213> ORGANISM: Artificial Sequence
<220> FEATURE:
<223> OTHER INFORMATION: synthetic polynucelotide

<400> SEQUENCE: 13
ccttctcgag cttggctcca ggtcagctc             29

<210> SEQ ID NO 14
<211> LENGTH: 30
<212> TYPE: DNA
<213> ORGANISM: Artificial Sequence
<220> FEATURE:
<223> OTHER INFORMATION: synthetic polynucelotide

<400> SEQUENCE: 14
ccttctcgag gaggctgatg gctaagcagt             30

<210> SEQ ID NO 15
<211> LENGTH: 26
<212> TYPE: DNA
<213> ORGANISM: Artificial Sequence
<220> FEATURE:
<223> OTHER INFORMATION: synthetic polynucelotide

<400> SEQUENCE: 15
caggtaccta acagggtatt tcccag             26

<210> SEQ ID NO 16
<211> LENGTH: 33
<212> TYPE: DNA
<213> ORGANISM: Artificial Sequence
<220> FEATURE:
<223> OTHER INFORMATION: synthetic polynucelotide

<400> SEQUENCE: 16
agtacagatg actttagctg gagagctgca cct             33

<210> SEQ ID NO 17
<211> LENGTH: 33
<212> TYPE: DNA
<213> ORGANISM: Artificial Sequence
<220> FEATURE:
<223> OTHER INFORMATION: synthetic polynucelotide

<400> SEQUENCE: 17
aggtgcagct ctccagctaa agtcatctgt act             33

<210> SEQ ID NO 18
<211> LENGTH: 30
<212> TYPE: DNA
<213> ORGANISM: Artificial Sequence
<220> FEATURE:
<223> OTHER INFORMATION: synthetic polynucelotide

<400> SEQUENCE: 18
tacagcctca tccctctctc tttcttcccc                                    30

<210> SEQ ID NO 19
<211> LENGTH: 30
<212> TYPE: DNA
<213> ORGANISM: Artificial Sequence
<220> FEATURE:
<223> OTHER INFORMATION: synthetic polynucelotide

<400> SEQUENCE: 19
ggggaagaaa gagagaggga tgaggctgta                                    30

<210> SEQ ID NO 20
<211> LENGTH: 32
<212> TYPE: DNA
<213> ORGANISM: Artificial Sequence
<220> FEATURE:
<223> OTHER INFORMATION: synthetic polynucelotide

<400> SEQUENCE: 20
acctgttgat agcagaacaa ggaataaggt ct                                 32

<210> SEQ ID NO 21
<211> LENGTH: 32
<212> TYPE: DNA
<213> ORGANISM: Artificial Sequence
<220> FEATURE:
<223> OTHER INFORMATION: synthetic polynucelotide

<400> SEQUENCE: 21
agaccttatt ccttgttctg ctatcaacag gt                                 32

<210> SEQ ID NO 22
<211> LENGTH: 30
<212> TYPE: DNA
<213> ORGANISM: Artificial Sequence
<220> FEATURE:
<223> OTHER INFORMATION: synthetic polynucelotide

<400> SEQUENCE: 22
ggatcaggaa tttagcttct gctttactga                                    30

<210> SEQ ID NO 23
<211> LENGTH: 30
<212> TYPE: DNA
<213> ORGANISM: Artificial Sequence
<220> FEATURE:
<223> OTHER INFORMATION: synthetic polynucelotide

<400> SEQUENCE: 23
tcagtaaagc agaagctaaa ttcctgatcc                                    30

<210> SEQ ID NO 24
<211> LENGTH: 24
<212> TYPE: DNA
<213> ORGANISM: Artificial Sequence
<220> FEATURE:
<223> OTHER INFORMATION: synthetic polynucelotide

```
<400> SEQUENCE: 24
tctcacaatt ttatggatca ggaa                                          24

<210> SEQ ID NO 25
<211> LENGTH: 20
<212> TYPE: DNA
<213> ORGANISM: Artificial Sequence
<220> FEATURE:
<223> OTHER INFORMATION: synthetic polynucelotide

<400> SEQUENCE: 25
caccaggcac cagagtacag                                               20
```